United States Patent [19]

Baumgartner

[11] 4,300,243
[45] Nov. 17, 1981

[54] PROCESS FOR THE PREPARATION OF PRESERVED TRANSPLANTS

[75] Inventor: Ludwig Baumgartner, Nuremberg, Fed. Rep. of Germany

[73] Assignee: Pfrimmer & Co., Pharmazeutische Werke Erlangen GmbH, Erlangen, Fed. Rep. of Germany

[21] Appl. No.: 119,613

[22] Filed: Feb. 8, 1980

[30] Foreign Application Priority Data

Feb. 21, 1979 [DE] Fed. Rep. of Germany ....... 2906650

[51] Int. Cl.³ .......................... A61F 1/00; A61F 1/24; F26B 3/00; F26B 5/04
[52] U.S. Cl. .................................................. 3/1; 34/9; 34/15; 3/1.4; 128/DIG. 8

[58] Field of Search ......................... 34/9, 15; 3/1, 1.4; 128/DIG. 8

[56] References Cited

U.S. PATENT DOCUMENTS 2,106,261  1/1938  Weidemann ........................... 39/9 X
2,659,986  11/1953  Hink, Jr. .................................... 34/9

FOREIGN PATENT DOCUMENTS 942226  11/1963  United Kingdom ......... 128/DIG. 8

Primary Examiner—John J. Camby
Attorney, Agent, or Firm—Jordan and Hamburg

[57] ABSTRACT

Biological collagenous material is preserved by dehydrating utilizing an organic water-miscible solvent.

14 Claims, No Drawings

PROCESS FOR THE PREPARATION OF PRESERVED TRANSPLANTS

BACKGROUND OF THE INVENTION

This invention relates to a process for the preparation of preserved transplants by dehydrating biological collagenous material.

In order to replace biological tissues, for instance skin, sinews, vessels, nerves, dura mater etc. presently autological tissues, in other words tissues arising from the same patient are being used. In order to produce them a second operation of the already weakened patient is in order, needing furthermore aseptical work and a large expenditure of time. An alternative to such a second operation may be found in the use of ready-made homologous or heterologous preserved tissue which may be used any time by the surgeon.

Freeze drying is a well known method for the preparation of biological transplants. In that case the water containing collagenous material is frozen at about $-25°$ C. and the water contained therein in the form of ice is removed by sublimation in vacuo. This method yields a collagenous tissue material containing a small percentage of water only, which may be kept in a sterile state as long as desired while keeping all its properties and may be used ready-for-use. The method of freeze-drying has several disadvantages when used for the preservation of planar materials.

Collagen is a structural protein, its fibrillar tissue swells when moist which causes an increase in thickness. The deep freezing so to say fixates the swollen state of the collagenous tissue. In case of a planar collagenous material, the dura mater for instance, a relatively thick spongy material results, the handling of which is restricted when used as a transplant. Its thickness, for instance amounts to 0.66 mm.

Ice crystals arising between the fibers and the fibrils loosen the collagenous fiber combination. The histological image shows clearly the difference between a freeze dried collagenous tissue and the respective tissue in its primary native condition. Due to the formation of ice crystals and the consecutive sublimation hollow spaces arise within the tissue, thereby changing its properties, elasticity for instance, compared to that of the native tissue. It worsens and is for native dura mater, for instance 1.8 kp, and for freeze dried dura mater, for instance 0.88 kp.

An additional criterion for the quality of a transplant particularly for prostethic plastics is the quality of the inner surface. The inner surface is graded according to its freeness of fibrils and fibers. The greater the freeness in other words the less partial adhesion or fusion of fiber to fiber occurs, the greater is the inner surface. The ideal exposure of the tissue is characterized by having a surface of about 20 $m^2/g$. The value for the inner surface is therefore an important criterion, because the transplanted tissue net functions better as a guiding means or grating for the ingrowing connective tissue, the more free fibers and fibrils occur in parallel regularity.

Due to the partial adhesion together of fibers and fibrils the inner surface of freeze dried Durakonserve (preserved dura mater) amounts to 5 to 10 $m^2/g$ (measured by the nitrogen adsorption method).

Another method uses chemical preservation by Cialit. In that case the biological tissue is stored in an aqueous medium containing, for example 0.05% Cialit. A disadvantage of this method is that chemical substances adhere to the tissue which will be transferred to the locus of the operation.

SUMMARY OF THE INVENTION

Due to the above disadvantages of these known methods, it is an object of the present invention to provide a method which either completely preserves the properties of a transplant when conserved, or at least adversely affects the properties of a collagenous transplant as little as possible.

Surprisingly, it was found that the desired properties of a collagenous tissue, the dura mater, for instance, are substantially conserved when dehydration is obtained by means of solvents miscible with water. The process is particularly economical because it needs substantially less outlay for apparatus in comparison to the freeze drying process.

DESCRIPTION OF THE PREFERRED EMBODIMENTS

Solvent dehydration according to the method of the invention results in shrinking of the tissue according to the amount of water removed. Thereby, there results, for instance in the case of a planar tissue like the dura mater, a thin compact transplantate material. Its thickness, for instance amounts to 0.47 mm. Due to the undamaged structure of the multidirectional fiber mat, the tissue is not loosened by any vacuoles resulting in a material easily handled by the surgeon due to its general good properties, like its low thickness and its flexibility.

The process according to the invention for the preparation of preserved transplants makes possible a dehydration and a freeing down to the fine structure of the fibrils of the collagenous tissue that prevents an adhesion together of fibrils and fibers. Due to the optimum freeing of fibers and fibrils the biological material, dura mater for instance, shows in its histological image a morphological structure very similar to the native tissue.

Thus properties are obtained which correspond very well to the properties of the native tissue. Practically, the elasticity is conserved and the extensibility is simultaneously quite negligible. The limit of elasticity amounts, for instance to 1.45 kp.

These properties determine the use of transplant preserves, prepared according to the invention as an ideal material for substitution plastic surgery, for instance for covering of defects of the abdominal wall.

The process for the preparation of preserved transplant by the aid of organic water-miscible solvents shows, compared to hitherto known methods, a series of advantages because it is suitable for the preservation of biological collagenous materials, like skin, vessels, nerves, sinews, fasces cartilage, dura mater etc.

It is particularly advantageous to use as dehydrating means the following solvents: ethanol, propanol, methanol, isopropanol, acetone, or methylethylketone or mixtures of these solvents.

In one particular embodiment of the invention the dehydration is actuated continually in a countercurrent system. By that, continually new solvent is brought in which therefore shows a high acceptance for the water to be extracted.

On the other hand it is also advantageously possible to proceed with the dehydration discontinually in several steps. In that case the transplant tissue remains, for instance for a certain interval in a first vessel with a solvent and is furtheron reacted in another vessel with the same solvent or another solvent, once the capability of the first solvent to extract water is reduced. Other steps may be added according to the needs until the desired final stage has been reached.

It was shown to be favorable to let the dehydration process last 2 to 24 hours, preferrably 5 to 12 hours.

Advantageously, drying of the collagenous transplant, containing solvent occurs at low pressures between 0.1 bar and 0.95 bar, preferrably at 0.5 bar. The lowering of pressure compared to atmospheric pressure speeds up the evaporation of the solvent and thereby the drying process.

On the other hand it may be advantageous from the point of view of economy of the process to run the drying process at ambient or atmospheric pressure.

Finally, the drying of solvent containing collagenous transplant may occur according to the invention at temperatures from 10 to 70° C., preferrably at about 37° C. The temperature of about 37° C. corresponds to the temperature of the human body so that it may be certain that the tissue be not exposed to thermal damages.

The process for the preparation of transplant preserves according to the invention may be illustrated according to the following examples:

EXAMPLE 1

The biological tissue, dura mater for example, was taken from a human body and freed by appropriate methods of antigens and enzymes. In order to preserve the tissue pieces, thus cleansed, they were treated by immersing them three times in a water-miscible organic solvent, for instance acetone, each immersion lasting 12 hours. Here the solvent used amounted to 500% of the wet weight of the tissue. The pieces of dura mater were removed from the last solvent bath and dried at a reduced pressure of 0.5 bar.

The dehydrated dura mater had a water content of 5%. Its thickness was 0.45 mm, the inner surface 21 m² per gram, and the limit of elasticity 1.40 kp. In a histological study the preserved material showed a structure substantially identical to the structure of native material, and the fibers were not loosened by interstitial vacoules.

After packaging in moisture-proof plastic or aluminum bags and sterilization by gammar rays with a minimum dose of 2.5 Mrad, the dura mater preserved had practically unlimited shelf-life and was ready-for-use when needed for transplanting.

EXAMPLE 2

Tendons taken from human or animal bodies were cleansed according to Example 1. Six consecutive immersions in isopropanol dehydrated the tissue. The tendon pieces remained each time for 10 hours duration in the alcohol bath. Isopropanol was used at a rate of 500% of the wet weight of the tissue. After removal from the last alcohol bath the tendon pieces were freed of isopropanol by exposure to a pressure of 0.5 bar, the material containing 10% water.

EXAMPLE 3

Fascialata removed from a human body were appropriately cleansed of antigens and enzymes like in Example 1. In order to preserve it, the fascialata was dehydrated each time for 5 hours in three isopropanol baths in tandem. Each time 500% of the wet weight of the fascialata was used for dehydration.

Fascialata thus treated was removed from the last bath and dried at atmospheric pressure and room temperature.

A water content of 9% resulted. The transplant was packaged in moisture-proof bags and irradiated with 2.5 Mrad.

In that state the fascialata preserve had practically a limitless shelf-life and was ready for use for transplants.

The parameters mentioned in the Examples may be varied by appropriate changes of the conditions mentioned in the examples relative to time, amounts etc. The described processes are to be understood as examples only.

What is claimed is:

1. A process for the preparation of biological collagenous material for use as a transplant comprises contacting said material in a continuous manner with fresh amounts of a water-miscible organic solvent selected from the group consisting of methanol, ethanol, propanol, isopropanol, acetone, methylethylketone and mixtures thereof so as to dehydrate said material, and subsequently removing said solvent at a pressure of between 0.1 bar to 1.0 bar.

2. A process according to claim 1, comprising effecting said dehydration in from 2 to 24 hours.

3. A process according to claim 2, comprising effecting said dehydration in from 5 to 12 hours.

4. A process according to claim 1, wherein after contacting said material with said solvent, said solvent is removed at a pressure of about 0.5 bar.

5. A process according to claim 1, wherein after contacting said material with said solvent, said solvent is removed at a temperature of from 10 to 50 degrees centigrade.

6. A process according to claim 5, wherein said solvent is removed at about 37 degrees centigrade.

7. A method of preserving material suitable for use as a human transplant comprising contacting dura mater with fresh amounts of water-miscible organic solvent selected from the group consisting of methanol, ethanol, propanol, isopropanol, acetone, methyl-ethylketone and mixtures thereof so as to dehydrate said dura mater, and subsequently removing said solvent at a pressure of between 0.1 bar and 1.0 bar.

8. Dura mater which has been preserved for use as a human transplant by contacting said dura mater in a continuous manner with fresh amounts of a water-miscible organic solvent selected from the group consisting of methanol, ethanol, propanol, isopropanol, acetone, methylethylketone and mixtures thereof so as to dehydrate said dura mater, and subsequently removing said solvent at a pressure of between 0.1 bar and 1.0 bar.

9. A method of preserving material suitable for use as a human transplant comprising contacting a biological collagenous material without subdivision thereof at ambient temperatures in the absence of added water with fresh amounts of water-miscible organic solvent selected from the group consisting of methanol, ethanol, propanol, isopropanol, acetone, methylethylketone and mixtures thereof so as to dehydrate said material, and subsequently removing said solvent at a pressure of between 0.1 bar and 1.0 bar, the final water content of said material being from 5 to 10%.

10. The method of claim 9 wherein said biological collagenous material is dura mater.

11. The method of claim 10 wherein, as a final step, the dehydrated dura mater is packaged in moisture-proof bags and irradiated with 2.5 Mrad.

12. A biological collagenous material which has been preserved for use as a human transplant by contacting said material without subdivision thereof at ambient temperatures in the absence of added water with fresh amounts of water-miscible organic solvent selected from the group consisting of methanol, ethanol, propanol, isopropanol, acetone, methylethylketone and mixtures thereof so as to dehydrate said material, and subsequently removing said solvent at a pressure of between 0.1 bar and 1.0 bar, the final water content of said material being from 5 to 10%.

13. The product of claim 12 wherein said biological collagenous material is dura mater.

14. The product of claim 13 wherein, as a final step in its preservation, the dehydrated dura mater is packaged in moisture-proof bags and irradiated with 2.5 Mrad.

* * * * *